United States Patent

Devaney, Jr.; Mark J. et al.

Patent Number: 5,460,780
Date of Patent: Oct. 24, 1995

[54] TEMPERATURE CONTROL DEVICE AND REACTION VESSEL

[76] Inventors: Mark J. Devaney, Jr.; Jeffrey A. Wellman; John S. Lercher, all of Eastman Kodak Co., Rochester, N.Y. 14650-2201

[21] Appl. No.: 452,932

[22] Filed: Dec. 18, 1989

Related U.S. Application Data

[63] Continuation-in-part of Ser. No. 365,079, Jun. 12, 1989, abandoned.

[51] Int. Cl.$^6$ .................................................. B01L 7/00
[52] U.S. Cl. .............................. 422/99; 422/68.1; 422/88; 935/77; 935/78
[58] Field of Search .................................. 422/55, 58, 66, 422/68.1, 98, 89; 435/6, 91; 935/77, 78

[56] References Cited

U.S. PATENT DOCUMENTS

3,036,894  5/1962  Forestiere .
3,620,678  11/1971  Gulgan et al. .................... 422/66
3,904,369  9/1975  Adler et al. ....................... 422/66
4,673,657  6/1987  Christian .
4,978,505  12/1990  Kertz .............................. 422/66

Primary Examiner—Timothy M. McMahon
Attorney, Agent, or Firm—Dana M. Schmidt

[57] ABSTRACT

A combination is provided of a reaction vessel and apparatus for processing it. Preferably, the latter features a temperature control device comprising two surfaces to contact a reaction vessel sandwiched between them, a heater element being disposed on one side of one of the surfaces, a cavity being provided at the heater element, and pressure means for delivering cooling gas to the cavity and the heater element and for removing the air after it has cooled the heater element. Most preferably, there is further included means for providing relative movement between the control device and a reaction vessel so sandwiched between the two surfaces.

16 Claims, 7 Drawing Sheets

TEMPERATURE CONTROL DEVICE AND REACTION VESSEL

This application is a continuation-in-part of application of U.S. Ser. No. 365,079 filed on Jun. 12, 1989, now abandoned.

FIELD OF THE INVENTION

The invention relates to a device for heating and cooling a reaction vessel rapidly through various temperatures, and particularly those temperatures useful in PCR amplification.

BACKGROUND OF THE INVENTION

Polymerase chain reaction (PCR) technology permits nucleic acid material, such as DNA, often extracted from as little as a single cell, to be amplified to hundreds of millions of copies. This is important since prior to PCR technology it was virtually impossible to detect a single DNA strand. However, when a single DNA strand, such as the DNA produced by a human immunodeficiency virus (e.g., HIV-I, otherwise known to cause AIDS), is added to amplifying reagents that will amplify the DNA of choice, hundreds of millions of copies of that DNA can be obtained in a relatively short time. Technology further allows for the detection of the amplified nucleic acid material (DNA for example), using probes that hybridize to the amplified material of choice, such probes in turn either being immobilized or immobilizable to a solid support, such as a filter membrane, and/or being labeled for detection using enzymes or other moieties.

Conventionally, this has been done by amplifying the nucleic acid material in a stoppered plastic container until the desired number of copies have been formed. Thereafter, the container is reopened, such as by unstoppering, and either the amplified copies are withdrawn and transferred to detection apparatus, or detecting reagents are added to the container used for the amplification, so that detection is done in the same container.

It has been discovered that such a technique is unsatisfactory for convenient and widespread use of PCR technology, because aerosols are produced in the act of unstoppering and/or transfer of fluids. Such aerosols contain a few molecules of the amplified nucleic acid material, e.g., DNA. The aerosols then proceed to disperse within the environment. Normally, such few molecules in the environment are not of great concern. However, in theory, only one DNA molecule is needed to ruin by contamination other amplifying containers yet to be used for detection. That is, if the errant DNA molecule floats into or is carried, inadvertently, by an operator to another amplifying container yet to be used, that one molecule is all that is needed to provide the DNA needed for the next amplification. Needless to say, if the point of the next test is to see if a particular DNA is present (e.g., from HIV-I), and it is detected only because of the errant DNA and not that of the patient, the test is ruined. Thus, the very power of DNA amplification becomes the source of potential ruin of the tests. As a matter of fact, an entire lab has been proven to be contaminated by the unstoppering of just a few containers in which the sample has already been amplified. Although such a problem might be avoidable by using highly skilled and trained personnel who painstakingly minimize the aerosols produced, the need for such labor makes the technology impractical for general use.

The aforesaid problem has been solved by a containment cuvette, which as described and claimed in commonly-owned U.S. application Ser. No. 306,735 filed on Feb. 3, 1989, entitled "Containment Cuvette for PCR and Method of Use", can be a flexible pouch. Such pouch features wall materials that define a reaction compartment, one or both of the wall materials in the compartment being flexible.

Although such a pouch can be heated and cooled rapidly by a variety of devices through the numerous temperature changes known in the art to be needed to do PCR amplification, there has been a need prior to this invention for simple, inexpensive and yet efficient temperature control devices especially adapted to such rapid temperature changes. It has been found, for example, that thermal cycling by heating and cooling a metal block on which a pouch sits, is relatively slow and inefficient.

SUMMARY OF THE INVENTION

We have constructed a temperature control device that provides the efficient temperature changes needed for a PCR cuvette as noted above.

More specifically, in one aspect of the invention, there is provided an apparatus for processing a reaction vessel to cycle it through at least two temperature changes, the apparatus comprising means for heating at least one side wall of a selected portion of a suitable reaction vessel, means for actively cooling the heating means at repeated intervals, and means for moving one of said reaction vessel and said heating and cooling means in a prescribed path relative to the other of said reaction vessel and said heating and cooling means.

In another aspect of the invention, there is provided a temperature control device for providing rapid temperature changes in a reaction vessel, the device comprising two surfaces for contacting a reaction vessel sandwiched between them, at least one of the surfaces comprising a thermally conductive material, and further including in the control device a) a heater element disposed on the side of at least one surface material opposite to the side that is to contact a reaction vessel, b) a wall surface spaced from the side on which the heater element is disposed to define a cavity for providing air flow over the element, and c) cooling means in the wall surface for delivering cooling air to the cavity and the heating element and for removing air from the cavity that has flowed over the heating element.

In a further aspect of the invention, there is provided a combination of a flexible, collapsible reaction vessel and processing apparatus. The vessel comprises opposed side walls spaced apart at portions of the vessel to provide a compartment, and at least one liquid confined to the compartment, the side walls being sufficiently compliant as to conform the liquid-confining side walls to the surface of objects pressing thereagainst. The apparatus comprises a) means for heating at least one of the side walls, the heating means being mounted to press on the one side wall, b) cooling means for actively cooling the heating means and c) means for pressing the heating and said cooling means against said at least one side wall with sufficient force as to conform the one side wall to the surface of the heating and cooling means.

Accordingly, it is an advantageous feature of the invention that apparatus is provided that can efficiently, inexpensively and rapidly cycle the temperature of liquid in a containment pouch from about 95° C. to at least 55° C. to 70° C. and back to about 95° C., within ±1° C., in a time of from about 20 sec. to 1.75 min., with a short dwell time at each of said temperatures, and without internal sensors.

It is a further advantageous feature of the invention that apparatus is provided to accurately produce such temperature cycling repeatedly for hundreds of times.

Other advantageous features of the invention are that it is small in size and has low power requirements.

Still other advantageous features will become apparent upon reference to the following Description of the Preferred Embodiments, when read in light of the attached drawings.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DESCRIPTION OF THE PREFERRED EMBODIMENTS

The invention is described for preferred embodiments in which a PCR containment cuvette is being processed by the device, and in which both platens on opposite sides of the cuvette are heated and cooled. In addition, the invention is useful to heat and cool any kind of reaction vessel, whether or not used for PCR amplification, and with only one of the platens operative to effect temperature changes.

Figure 1:
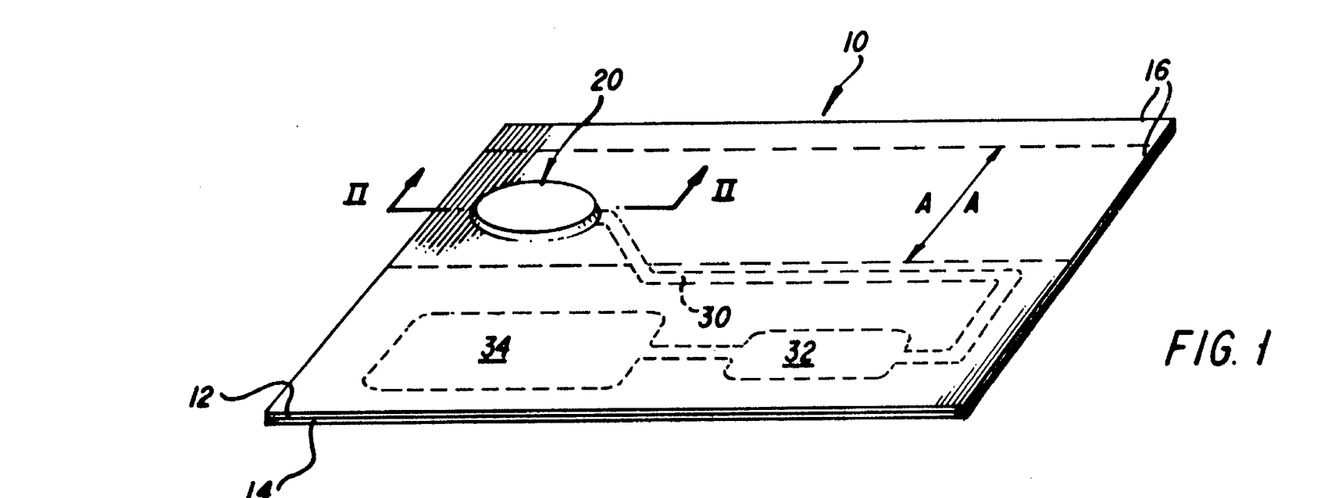
FIG. 1 is a perspective view of a simplified containment cuvette that can be processed by the device of this invention.
Figure 2:
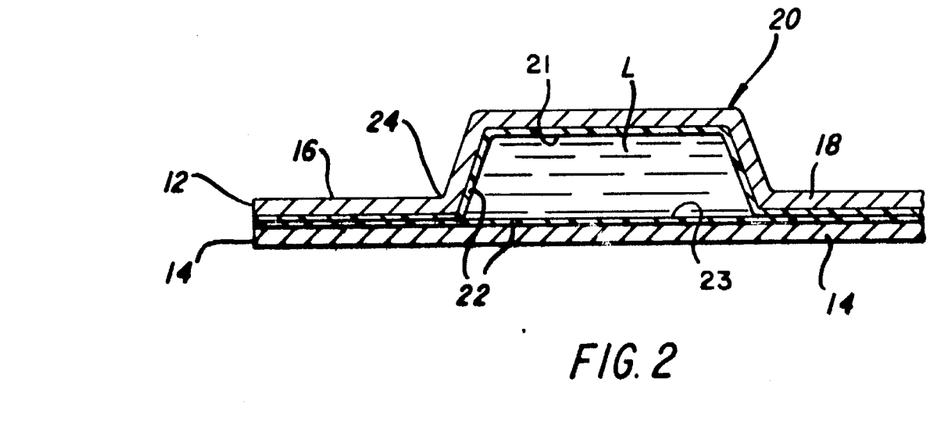
FIG. 2 is a fragmentary section view taken generally along the line II—II of FIG. 1.

Referring first to FIGS. 1 and 2, a preferred reaction vessel operated upon by the device of the invention comprises a flexible pouch 10 formed by preferably compliant, laminated sheets 12 and 14 sealed at least around the periphery 16. Sheets 12 and 14 can be formed, in at least the part thereof providing a reaction compartment 20, FIG. 2, of thermally conductive material 18, such as aluminum, over which a coat of a polymer 22 is preferably placed, to keep the aluminum from inhibiting the amplification. Preferably, however, sheets 12 and 14 are solely comprised of a flexible plastic. Most preferably, they comprise a sandwich of polyester and polyethylene or polypropylene, having a total thickness of between about 0.06 mm and 0.2 mm. Such thicknesses are useful as they insure that the wall is sufficiently thermally conductive, even in the absence of a layer of aluminum. It is important that, whatever the materials selected, the sheets be compliant enough to conform to the surfaces pressed against the opposite sidewalls of compartment 20, shown as side walls 21 and 23, FIG. 2. The two sheets are also heat-sealed around compartment 20 at edge 24, so that a sample liquid L can be introduced by a passageway (not shown) that is then sealed, and retained for processing. As shown, the protrusion of compartment 20 occurs only in sheet 12, but it can also occur in sheet 14. To provide selective bursting, a weakened heat seal is provided between the two sheets 12 and 14 to create a future flow passageway 30 that delivers liquid to a detection compartment 32 containing detection reagents suitably introduced, and then to a waste compartment 34. (That is, a storage compartment can also be provided, not shown, similar to compartment 20 but containing liquid reagents.) Dotted line A—A represents the path that pressure means are to travel over cuvette 10, after suitable heating and cooling of compartment 20, to compress at least compartment 20 to force liquid to flow out to compartment 32.

Figures 3, 6:
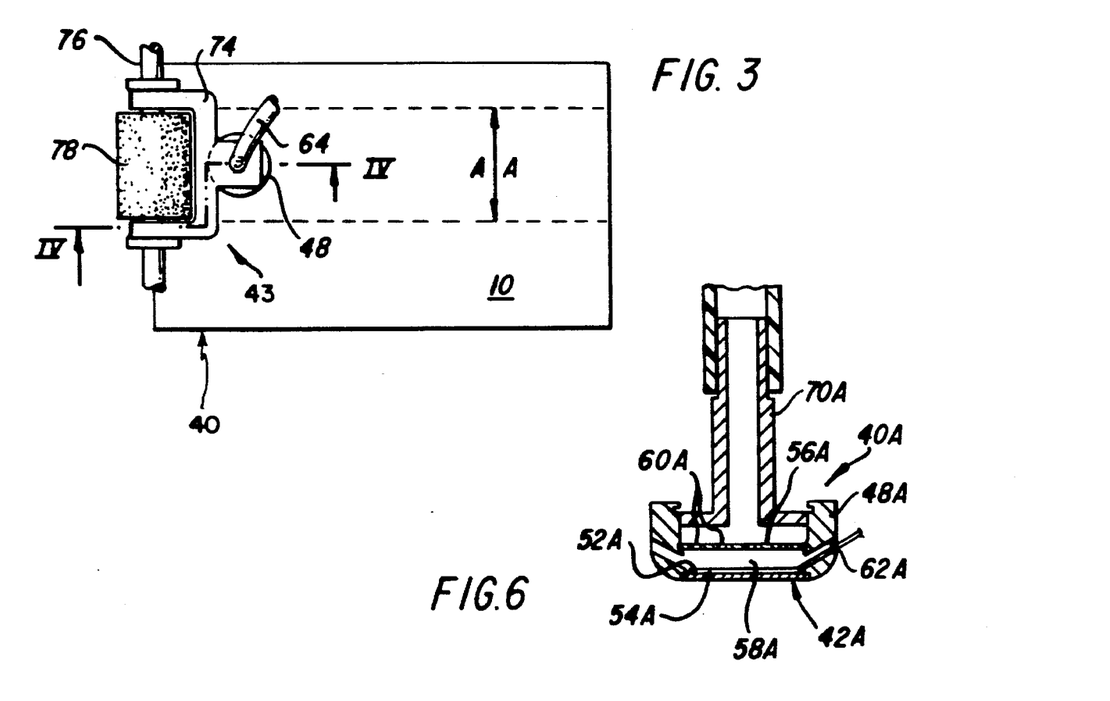
FIG. 3 is a fragmentary plan view illustrating a temperature control device constructed in accord with the invention, with a cuvette of FIG. 1 in place.
FIG. 6 is a fragmentary view similar to a portion of FIG. 4, but illustrating an alternative embodiment.
Figure 4:
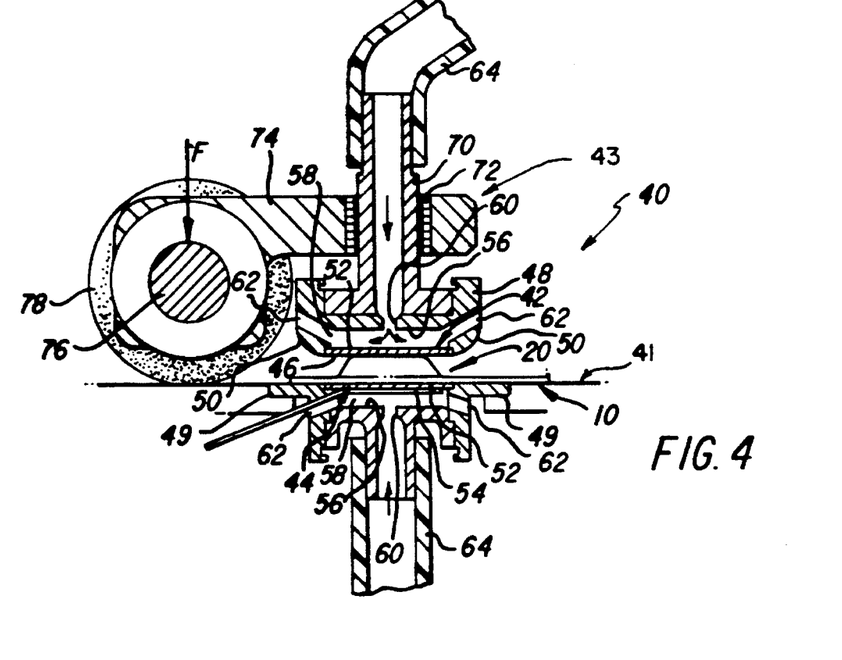
FIG. 4 is a section view taken generally along the line IV—IV of FIG. 3.

The device 40 of the invention that preferably does the temperature processing of compartment 20 appears in FIGS. 3–4. It comprises preferably a stationary support 41 and an upper member 43 that moves over the support. Alternatively, support 41 can be moved under member 43. Thus, device 40 comprises two opposed platens 42, 44, FIG. 4, having surfaces 46 that contact the cuvette, generally with the same area (here, circular) as the periphery of the compartment to be heated. Platens 42 and 44 are preferably thermally conductive material, such as aluminium. They can be grooved to allow trapped air to escape.

Platens 42 and 44 are preferably mounted in housing 48, 49, respectively. Housing 48 is mounted in support 41 and has its outer corners beveled at 50, for reasons that will become apparent. Housing 48 preferably comprises a material that is poorly conducting.

At least one of the two portions 41 and 43 has a heating means and preferably means for actively cooling the heating means. ("Active" is used herein to distinguish from passive cooling that always occurs when a heating force, e.g., electricity, is removed.) Thus, on side 52 of platens 42 and 44 that is opposite to side 46, a heating element 54 is disposed (not shown for platen 42 for clarity.) Such heating element is preferably a flexible, electrically driven device, such as a flexible printed circuit manufactured by Ocean State Thermotics, which can be operated at 24 volts D.C., to generate 20 watts of heat.

A conventional temperature sensor is preferably included (not shown), on surface 46 of platens 42. Useful sensors include thermocouple and RTD types.

The housing for each platen 42 and 46 has a wall surface 56 spaced away from the platen and its heating element, to define a gas flow cavity 58. To actively cool the heating element, wall surface 56 is then provided with preferably at least one jet inlet aperture 60, and at least one exhaust aperture 62. Preferably, inlet aperture 60 is disposed directly opposite to, and aimed at, heating element 54. The exhaust aperture(s) 62 are preferably several in number, disposed around the circumference of each platen. A gas hose 64 is fluidly connected to inlet aperture 60, whereas the exhaust apertures deliver the gas of cavity 58 to the atmosphere. Preferably, hose 64 delivers air (or an inert gas) at a pressure of between about 0.01 and about 0.35 kg/cm$^2$ Such active cooling provides the rapid decrease in temperature that is desired in reactions such as PCR amplification.

Housing 48 is mounted on a spindle 70, to allow relative movement of the platens towards and away from each other. Since platen 44 and housing 49 are preferably fixed, this requires spindle 70 to be movable away from and towards cuvette 10 that is disposed on platen 44. Preferably this is achieved by mounting spindle 70 in a sliding fit in bushing 72, mounted in a frame 74. Spindle 70 can then be raised and lowered by hand or by automatic means. Alternatively, it and platen 42 can be allowed to simply ride over the exterior surface of cuvette 10. Beveled corners 50 thus act to cam platen 42 upward when housing 48 encounters another protruding compartment.

Most preferably, frame 74 is a C-shaped yoke mounted to ride on an axle 76, FIGS. 3 and 4, that carries a pressure roller 78 journalled to axle 76. Axle 76 can then be caused to traverse cuvette 10 so that roller 78 follows path A—A, FIG. 3, albeit in a non-continuous motion that allows platens 42 and 44 to repeatedly heat and cool each compartment prior to rupture caused by roller 78. The traversal movement of axle 76 is either directed manually, or by automated means, not shown.

When compartments such as compartment 20 are to be compressed by roller 78 to force the liquid out into the other passageways, force F of about 1 to 7 kg/cm of roller length is preferably applied to axle 76, FIG. 4, for a roller that is about 4 cm long.

A conventional microprocessor is preferably used (not shown) to control the cycling of heating element 54 and the cooling hose 64.

When in use, the apparatus and the temperature control device are used to rapidly heat a selected portion of the reaction vessel, e.g., a containment compartment that is a reaction compartment, to the necessary high temperature, followed by a rapid cooling to a much lower temperature, achieved by the active cooling means. This is done repeatedly for as many cycles as is necessary for the desired reaction, while upper platen 42 stays in contact with the compartment. In the case of DNA replication by PCR technology, preferred cycling includes up to 50 repetitions, for example.

When the cycling is finished, the temperature control device 40 is moved out of its contact with the compartment, alone path A—A and relative to the reaction vessel, by rolling the roller. Preferably, the roller then advances into contact with the compartment in which the reaction took place, to burst it to send the contents therein to the next part of the vessel. Following this, device 40 continues on to other liquid-containing compartments in path A—A, not shown in FIG. 1. For at least some of the other compartments, repeated temperature cycling is not needed, in each case, so that little or no dwell time is spent by the heating platen over such compartments, and indeed the heater element is turned off. The roller, however, is effective to burst them to push the contents to, e.g., the detection chamber.

Figure 5:
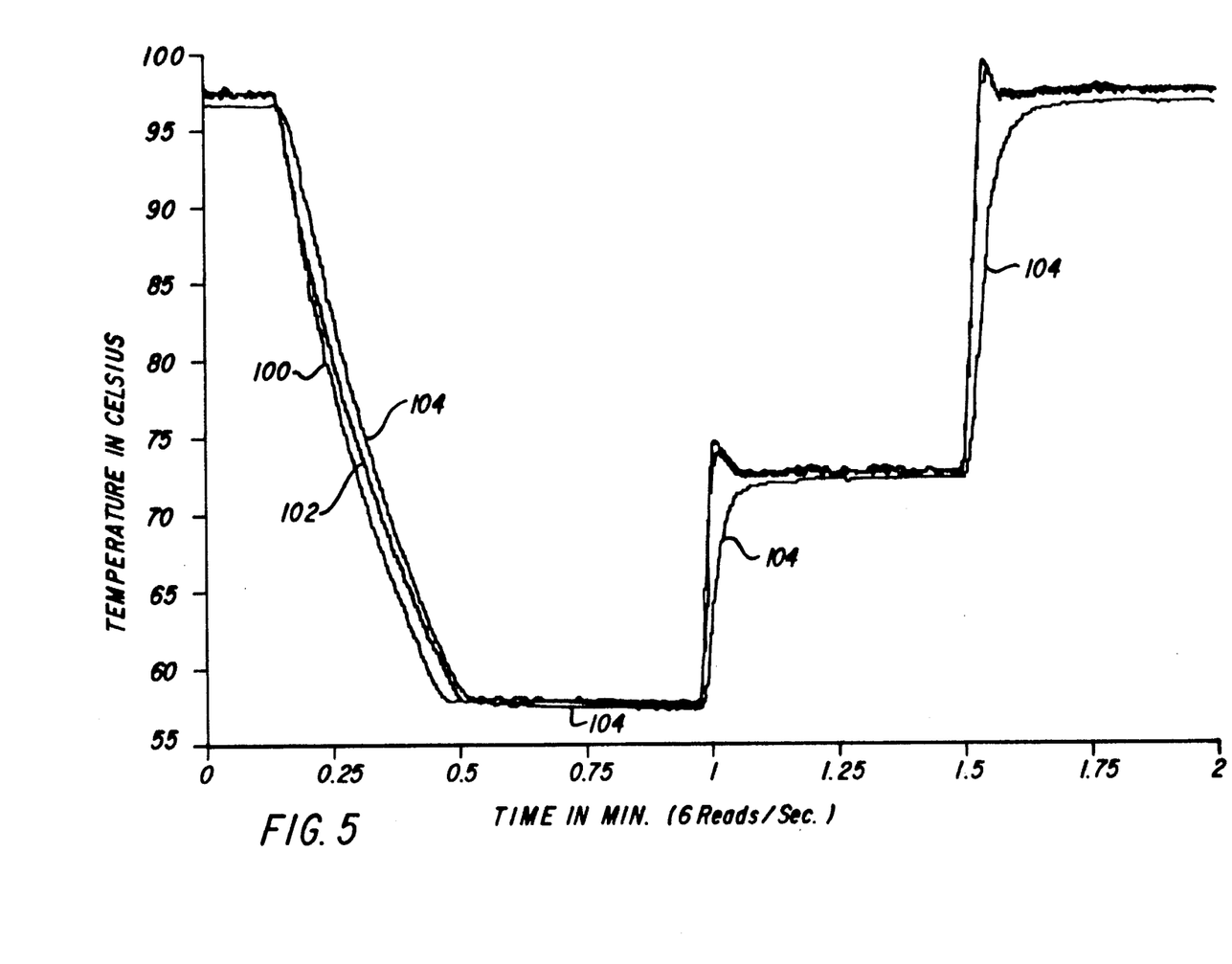
FIG. 5 is a graph of time and temperature produced by the device and cuvette of FIG. 3.

More specifically, using the device of this invention, a temperature response curve was obtained as is shown in FIG. 5. In this case, the compartment 20 was defined by polyester sheets 12 and 14 having a thickness of 63.5 microns (2.5 mil). The volume of the compartment was 140 μl, and it was 2.16 mm thick. The contents was mineral oil (for purposes of measuring temperature), and a thermocouple was inserted into the oil between sheets 12 and 14.

Trace 100 is the temperature that was delivered by platen 44, as measured by a temperature probe. Trace 102 is that of platen 42, and trace 104 is that of the oil inside compartment 20. Trace 104 shows a remarkable correlation and tracking for the temperature inside the compartment, compared to that of the platens, even through the drastic heating and cooling that occurs between about 57° C. about 97° C., and back again, all within the cycle time span of about 1.3 min. for the selected dwell times. (The temperature plateaus selected in this run correspond to desired temperatures for PCR amplification, as is well-known.) Faster cycling times have also been achieved—as fast as 45 seconds.

It is not essential that the jet inlet aperture be a single aperture, to cool off the heating element. Instead, it can be a plurality of apertures, as shown in FIG. 6. Parts similar to those previously described bear the same reference numeral to which the distinguishing suffix "A" has been appended.

Thus, the upper portion of device 40A (only part shown) has a platen 42A in housing 48A with a heating element 54A on surface 52A, as before. Spindle 70A provides air to chamber 58A, and exhaust apertures 62A remove the air. However, in this case there is a plurality of jet inlet apertures 60A, all in surface 56A that is spaced away from heating element 54A.

Figure 7:
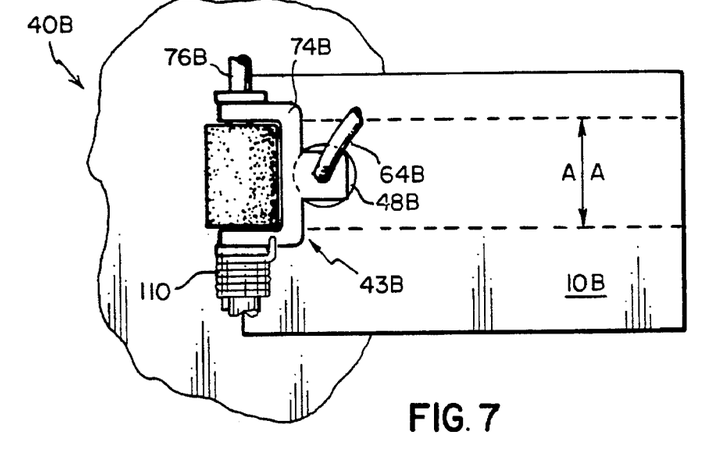
FIG. 7 is a plan view similar to that of FIG. 3, but illustrating still another alternate embodiment.
Figure 8:
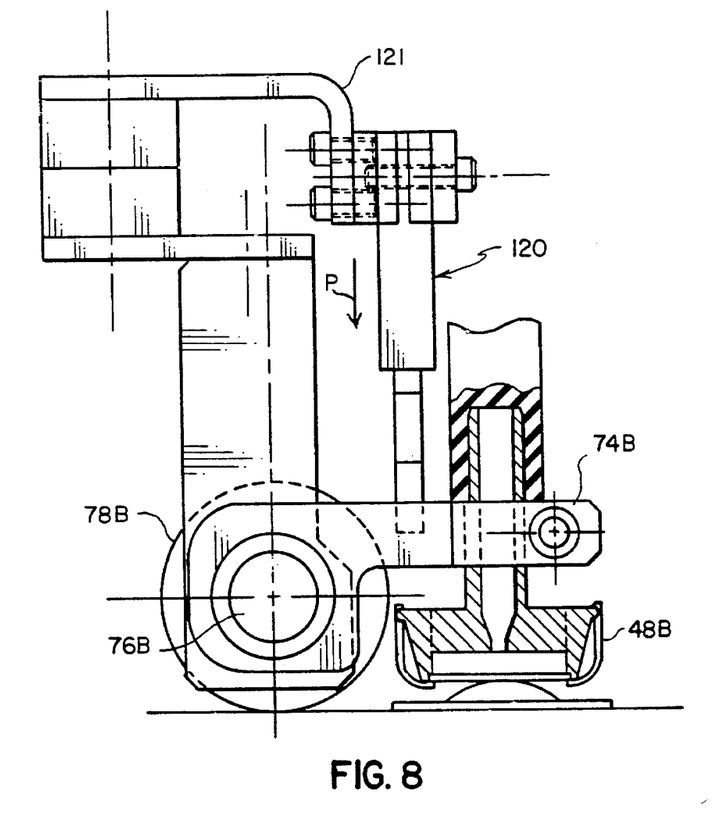
FIG. 8 is a partially sectioned view similar to FIG. 4 but of an alternate embodiment.

Most preferably, the upper heating and cooling means is applied with a certain force against the compliant pouch, to enhance contact and thus the heat conductivity. This in turn enhances the speed of the reactions therein, FIG. 7. Parts similar to those previously described bear the same reference numeral, to which a distinguishing suffix "B" is applied. Thus, FIG. 7, device 40B preferably comprises a stationary support 41B and an upper, movable member 43C, constrained to follow path A—A over a pouch or flexible reaction vessel 10B. Both support 41B and member 43B are generally constructed as described above. In addition, however, upper member 43B includes means 110 for applying a specific loading force against heater platen in housing 48B. As shown, such means is a torsion spring mounted on axle 76B, with a spring content selected to ensure the application of the desired force, as described hereinafter. Alternatively, this force applying means 110 can be, instead, additional selected mass mounted on the spindle to which hose 64B is connected, or even hydraulic means biasing yoke 74B to move downwardly relative to axle 76B with a predetermined force. For example, a piston 120 on frame 121 can be used to apply a variable, pre-selected pressure P, as shown in FIG. 8.

The amount of loading force needed for optimum compliance of the compartment side wall with the surface of the heating and cooling element, depends on the materials, the material thickness, and content of the compartment. The more flexible, thinner, and compliant each side wall is, the less is the force that is required. Preferably, the side walls and the loading force are selected to produce at least as much compliance of the side walls to the contacting surfaces, as occurs when about 270 g (0.6 pound) of loading force is applied by means 110 to the upper heating and cooling element 43, in contact with a compartment containing 170 ml of liquid and comprising two opposed compliant sheets each consisting essentially of a sandwich of about 0.013 mm thick polyester and about 0.1 mm thick polyethylene. This construction provides a surface area of contact that is about 180 mm².

Figure 9:
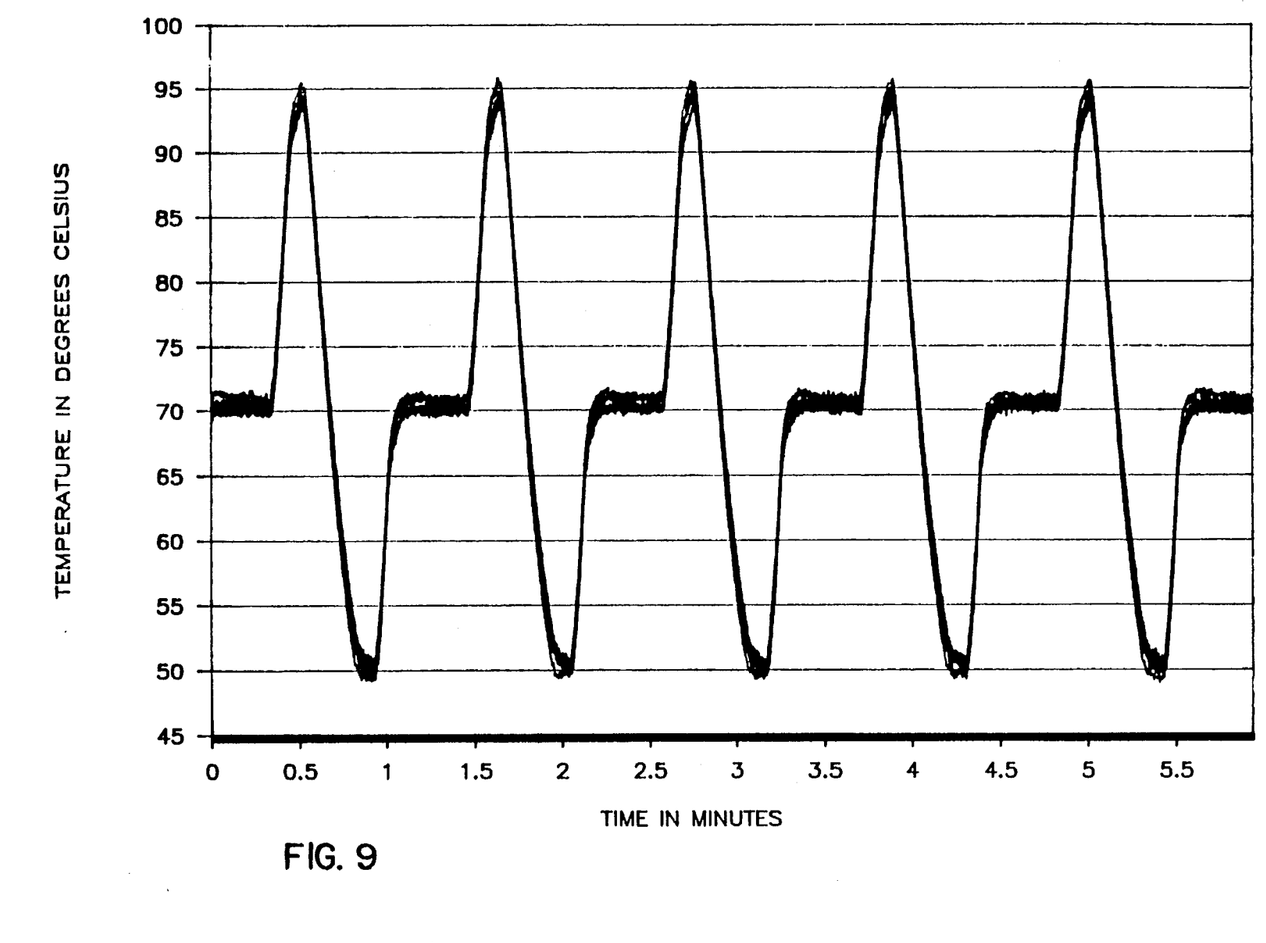
FIG. 9 is a plot of temperature and time achieved by the combination of this invention, for six different compartments processed as described, six traces which overlap to the degree shown.

Such compliance and the means that achieve it, have been found to produce extraordinary PCR reactions. Importantly, the contents of the heated and cooled compartment are constrained to better follow the temperature of the heating and cooling means in a repeatable fashion. This is essential since each thermal cycle must be exact in its limits to achieve DNA replication. The reproducibility of the cycles is demonstrated in FIG. 9, wherein the six curves each represent different compartments in six different reaction vessels, separately sequenced through the apparatus for at least five cycles using 227 of force. In each case, the contents' temperature was measured by an inserted temperature probe, and the volume of each compartment was, respectively 170–190 µ. The traces more or less overlap precisely. The result is that each compartment in each cycle reached a high temperature of at least about 93° C. and a low temperature of at least about 50° C., the ranges preferred for PCR processing.

Figure 10:
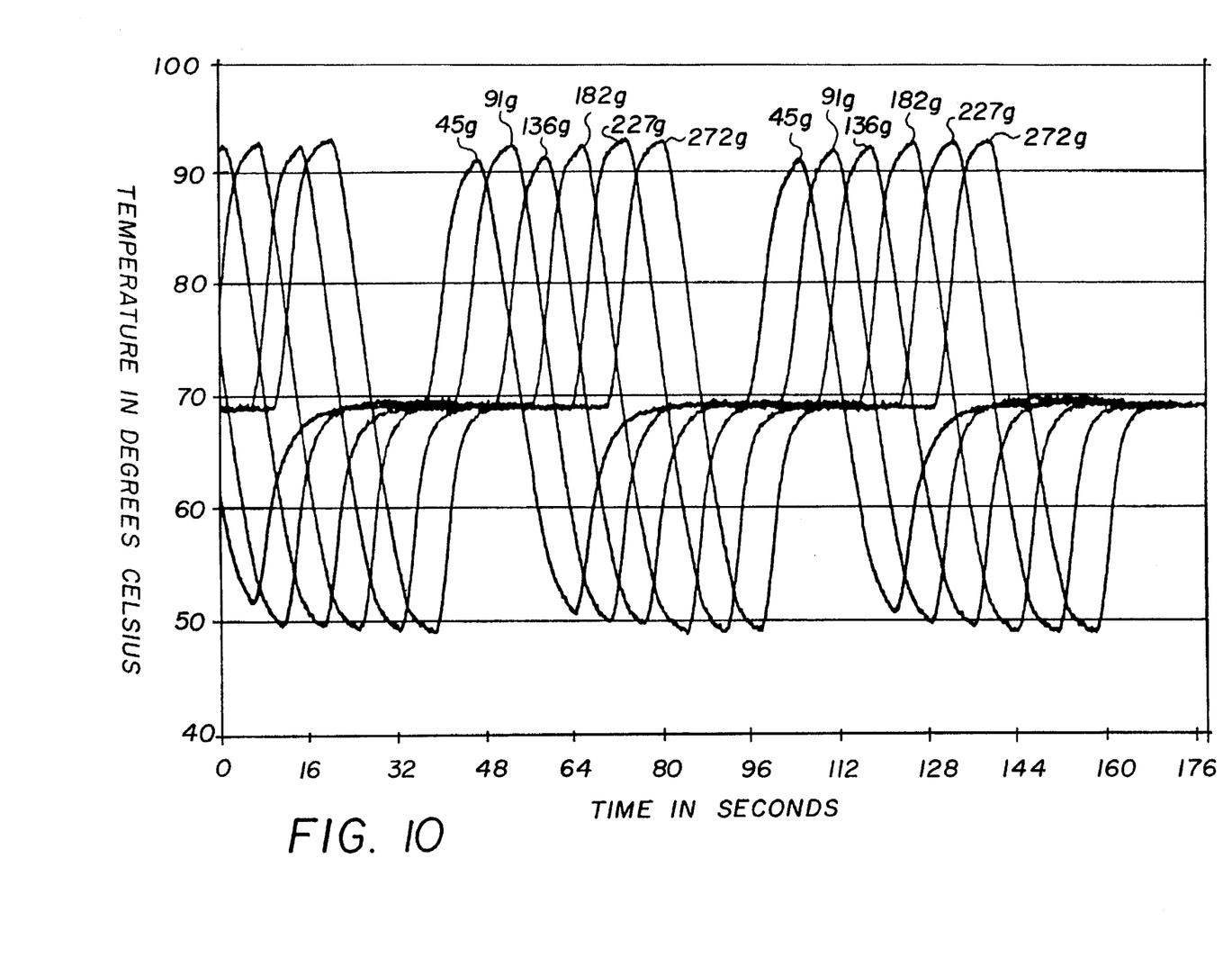
FIGS. 10 and 11 are each a plot of temperature vs. time similar to the plot of FIG. 8, except that each curve represents a different level of force exerted against the compliant compartment.

The difficulty of operating at forces less than 270 g can be seen from FIG. 10. For these results, each of the examples shown in FIG. 10 used a single compartment of the pouch comprising two sheets each consisting essentially of a sandwich of about 0.013 mm thick polyester and about 0.1 mm thick polyethylene, sealed to provide a confined volume that was substantially filled with about 170 ml of water, and then cycled on both sides with device 40B of FIG. 7, to achieve the temperatures noted in FIG. 10. The pressure applied by means 110 was varied to be the predetermined amount noted for each curve trace. Temperature was sensed inside the compartment. It was not until the force was at least about 270 g (the curve on the right-hand side of the group), for this compliant compartment, that the extreme temperatures of the cycle could be predictably achieved.

Most preferably, the force applied by means 110 and the compliability of the side walls is at least that achieved by applying at least 900 g of force to the compartment described. This extra force causes the temperature of the contents to track even faster, as is evident from FIG. 11, wherein the "flat" or double-peaked portions of the curve tops and valleys at 900 g or higher, indicate the desired end temperature is reached sooner. In these examples, the same procedure was followed as for FIG. 10, except that the force exerted by the upper heating and cooling means was one of those noted in FIG. 11. The "flat" portion occurs because both the heating means and the cooling means are preferably programmed to provide a flat constant temperature for a few seconds, for example, for about one sec, at the extremes of the cycled temperatures. This ensures that the liquid temperature predictably and repeatedly reaches the needed value. Only those compartments that reach these values in a timely fashion will demonstrate the constancy of that endpoint temperature. Apparatus and pouches processed in this manner are better able to control the PCR amplications.

It will be apparent that the upper limit on the amount of force applied by upper member 43, 43A or 43B is determined primarily by the amount of force effective to burst the reaction compartment. The force applied by member 43 is selected to be slightly less than this value, and the force applied by the following roller is slightly greater. The burst force of compartment 20, FIG. 1, can be, e.g., about 1800 g.

Figure 11:
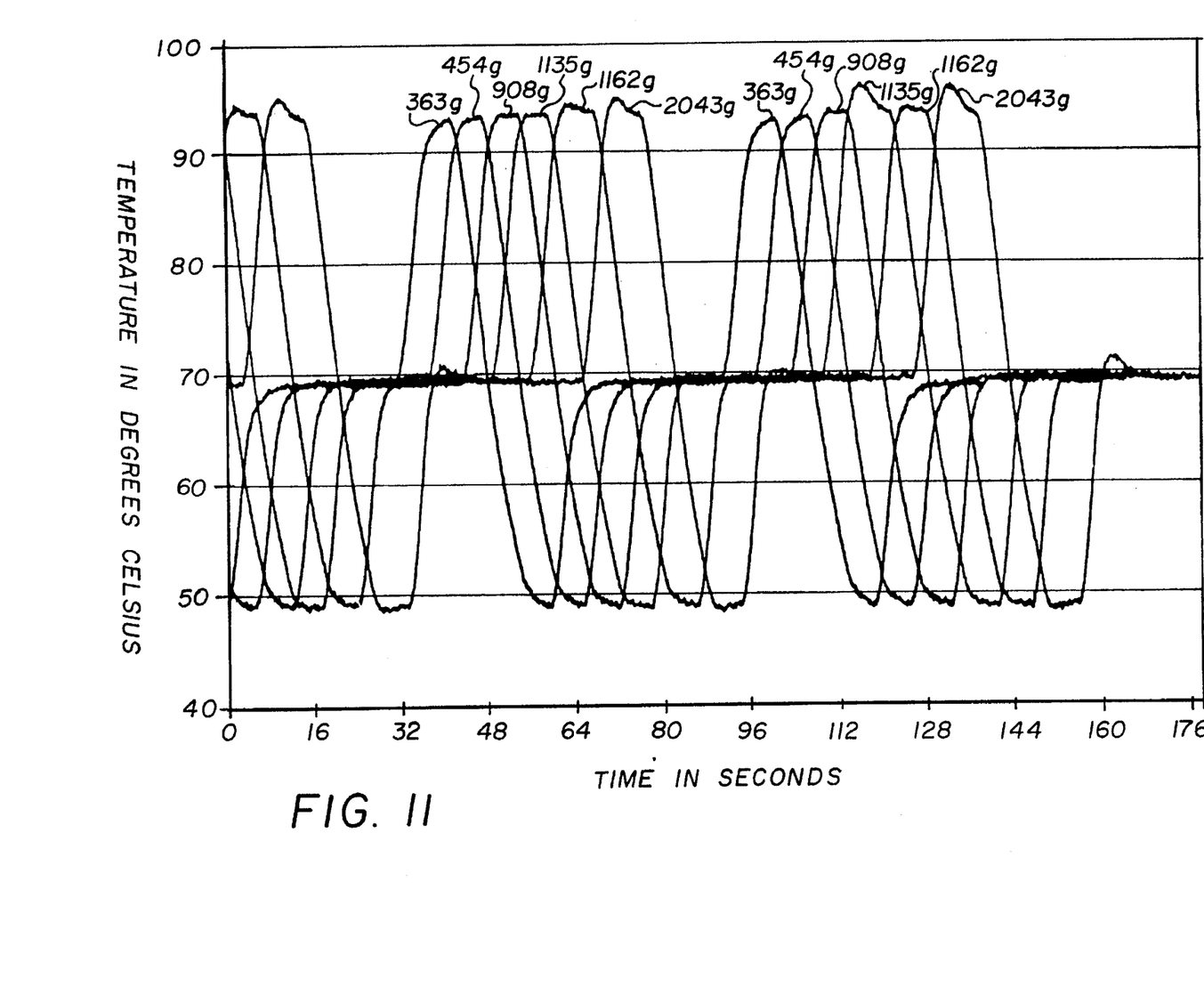

Some of the curves of FIG. 11 show a double peak at the curve tops. This occurs only because the heating element was programmed to overshoot the desired temperature—an unnecessary step when results such as those for the curves at 900 g or higher force, are achieved.

The previously-described embodiments feature the preferred use of the roller as the means for compressing and bursting the liquid-containing chambers. Any other mechanism can be used as well. For example, in FIG. 8, roller 78B can be omitted and instead piston 120 can be used to increase the pressure onto chamber 20B until it bursts, for example, at 1800 g of force to cause liquid to flow into the exit passageway (not shown).

The invention has been described in detail with particular reference to certain preferred embodiments thereof, but it will be understood that variations and modifications can be effected within the spirit and scope of the invention.

What is claimed is:

1. Apparatus for processing a flexible reaction vessel containing burstable compartments to cycle it through at least two temperature changes, the apparatus comprising:

means for heating at least one side wall of a selected portion of a suitable reaction vessel, means for actively cooling said heating means at repeated intervals, and means for moving one of a) said reaction vessel and b) said heating and cooling means in a prescribed path relative to the other of a) said reaction vessel and b) said heating and cooling means, said moving means comprising means for compressing and bursting selectively, said compartments of the flexible reaction vessel after it is heated and cooled by said heating means and said cooling means, respectively.

2. Apparatus for processing a flexible reaction vessel containing burstable compartments to cycle it through at least two temperature changes, the apparatus comprising:

means for heating at least one side wall of a selected portion of a suitable reaction vessel, means for actively cooling said heating means at repeated intervals, and means for moving one of a) said reaction vessel and b) said heating and cooling means in a prescribed path relative to the other of a) said reaction vessel and b) said heating and cooling means, said moving means comprising means for compressing and bursting selectively, said compartments of the flexible reaction vessel after it is heated and cooled by said heating means and said cooling means, respectively) said moving means and said compressing means comprising a roller mounted on a axle.

3. Apparatus as defined in claim 2 wherein said heating means and said cooling means are carried on said axle.

4. Apparatus as defined in claim 3, and further including mean for biasing said heating means and said cooling means against the selected reaction vessel portion with a predetermined force.

5. Apparatus as defined in claim 4 and wherein said biasing means is sufficient to compress the reaction vessel into a surface compliance with contacting objects that is at least equivalent to the compliance achieved when using about 270 g of force delivered over a generally circular area of about 180 mm² on a compartment in a reaction vessel, said compartment being comprised of opposed sidewalls each consisting essentially of a sandwich of about 0.013 mm thick polyester and about 0.1 mm thick polyethylene, and being substantially filled with about 170 µl of liquid.

6. Apparatus for processing a reaction vessel to cycle it through at least two temperature changes, the apparatus comprising:

means for heating at least one side wall of a selected portion of a suitable reaction vessel, means for actively cooling a said heating means at repeated intervals, and means for moving one of a) said reaction vessel and b) said heating and cooling means in a prescribed path relative to the other of a) said reaction vessel and b) said heating and cooling means, wherein said cooling means further comprise a jet aperture and a source of pressurized gas, said aperture and aligned with said heating means to cool it with said gas.

7. In combination, a flexible, collapsible reaction vessel comprising opposed side walls spaced apart at portions of the vessel to provide a compartment, and at least one liquid confined to said compartment, said side walls being sufficiently compliant as to conform said liquid-confining side walls to the surface of objects pressing thereagainst, and processing apparatus for said vessel, said apparatus comprising a) means for heating at least one of said side walls, said heating means being mounted to press on said one side wall, b) cooling means for actively cooling said heating means, and c) means for pressing said heating and said cooling means against said at least one sidewall with sufficient force as to conform said one side wall to the surface of said heating and cooling means.

8. A combination as defined in claim 8, wherein said force is at least about 270 g of loading when said compartment contains a liquid of about 170 μl and said side walls each consists essentially of a sandwich of about 0.013 mm thick polyester and about 0.1 mm thick polyethylene.

9. A combination as defined in claim 7 and further including in said apparatus, d) a generally flat support for said reaction vessel, and e) heating means in said support for heating the other of said side walls.

10. A combination as defined in claim 7, 8 or 9, and further including in said apparatus, a roller for compressing and bursting selectively, said compartment.

11. A combination as defined in claim 10, wherein said roller, and said heating and Cooling means for said at least one side wall are mounted on an axle.

12. A temperature control device for providing temperature changes in a reaction vessel, said device comprising two surfaces for contacting a reaction vessel sandwiched between them, at least one of said surfaces comprising a thermally conductive material, and further including in said control device a) a heater element disposed on a side of said at least one surface material, b) a wall surface spaced from said surface material to define a cavity for providing air flow over said element, and c) cooling means in said wall surface for delivering cooling air to said cavity and said heating element and for removing air from said cavity that has flowed over said heating element.

13. A device as defined in claim 12, in which both of said surfaces comprise said thermally conductive material, and there is further included with both of said surfaces on the side of the material opposite to the side that is to contact a reaction vessel, said heater element and said wall surface.

14. A device as defined in claim 12 or 13, wherein said cooling means comprise at least one jet aperture in said wall surface opposite to said heater element, and at least one exhaust aperture disposed to one side of said heater element, said jet aperture being fluidly connected to an air source and said exhaust aperture being fluidly connected to the atmosphere.

15. A device as defined in claim 12 or 13, in which at least one of said surfaces is mounted on a movable frame, and further including means for moving said frame across a reaction vessel disposed between said surfaces.

16. A device as defined in claim 15, and further including on said frame, a roller for compressing a reaction vessel against the other of said surfaces not mounted on said frame.

* * * * *

UNITED STATES PATENT AND TRADEMARK OFFICE
CERTIFICATE OF CORRECTION

PATENT NO. : 5,460,780
DATED : October 24, 1995
INVENTOR(S) : Devaney, Jr.; Mark J. et al It is certified that error appears in the above-indentified patent and that said Letters Patent is hereby corrected as shown below:

Column 8, Line 44, after "means," delete "respectively)" and insert --respectively--.

Column 8, Line 46, after "mounted on" delete "a" and insert --an--.

Column 8, Line 50, after "further including", from Line 49, delete "mean" and insert --means--.

Column 9, Line 1, after "cooling" delete "a".

Column 9, Line 8, after "aperture" delete "and" and insert --being--.

Column 9, Line 22, after "one" delete "sidewall" and insert --side wall--

Column 10, Line 2, after "heating and" delete "Cooling" and insert --cooling--.

Signed and Sealed this

Ninth Day of April, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,460,780
DATED : October 24, 1995
INVENTOR(S) : Mark J. Devaney, Jr. Jeffrey A. Wellman, John S. Lercher It is certified that error appears in the above-indentified patent and that said Letters Patent is hereby corrected as shown below:

On the title page: Item [73] Assignee should read -- Clinical Diagnostic Systems, Inc. --.

Signed and Sealed this

Twenty-fifth Day of June, 1996

Attest:

BRUCE LEHMAN

Attesting Officer     Commissioner of Patents and Trademarks

UNITED STATES PATENT AND TRADEMARK OFFICE
CERTIFICATE OF CORRECTION

Patent No.: 5,460,780

Dated: October 24, 1995

Inventors: Mark J. Devaney, Jr.
Jeffrey A. Wellman
John S. Lercher

It is certified that error appears in the above-identified patent and that said Letters Patent is hereby corrected as shown below:

Column 4, Line 59, after "42," insert --and 44--.

Column 4, Line 61, after "and" delete "46" and insert --44--.

Signed and Sealed this

Sixth Day of May, 1997

*Attest:*

*Attesting Officer*

BRUCE LEHMAN

*Commissioner of Patents and Trademarks*